(12) United States Patent
Doll

(10) Patent No.: US 8,083,398 B2
(45) Date of Patent: Dec. 27, 2011

(54) SENSOR ARRANGEMENT

(75) Inventor: Wolfgang Doll, Leinfelden-Echterdingen (DE)

(73) Assignee: SITRONIC Ges.fuer elektrotechnische Ausruestung mbH & Co. KG, Gaertringen (DE)

( * ) Notice: Subject to any disclaimer, the term of this patent is extended or adjusted under 35 U.S.C. 154(b) by 524 days.

(21) Appl. No.: 12/313,840

(22) Filed: Nov. 25, 2008

(65) Prior Publication Data

US 2010/0128751 A1    May 27, 2010

(30) Foreign Application Priority Data

Nov. 28, 2007  (DE) .......................... 10 2007 047 888

(51) Int. Cl.
*G01N 25/68* (2006.01)

(52) U.S. Cl. ..................... 374/28; 374/E1.001; 340/521

(58) Field of Classification Search .................. 374/28, 374/45, E1.001; 340/521, 5.52
See application file for complete search history.

(56) References Cited

U.S. PATENT DOCUMENTS

| | | | | |
|---|---|---|---|---|
| 4,626,774 A * | 12/1986 | Regtien | .......................... | 324/683 |
| 4,801,211 A * | 1/1989 | Yagi et al. | ........................ | 374/28 |
| 5,105,191 A * | 4/1992 | Keedy | .............................. | 340/968 |
| 6,795,871 B2 * | 9/2004 | Nolan et al. | ........................ | 710/8 |
| 6,992,580 B2 * | 1/2006 | Kotzin et al. | ............. | 340/539.11 |
| 7,148,796 B2 * | 12/2006 | Joy et al. | .......................... | 340/521 |
| 7,173,538 B2 * | 2/2007 | Pedraza et al. | ................ | 340/604 |
| 7,403,126 B2 * | 7/2008 | Pedraza et al. | ................ | 340/604 |
| 7,456,733 B2 * | 11/2008 | Joy et al. | ........................ | 340/521 |
| 2003/0009610 A1 * | 1/2003 | Nolan et al. | ...................... | 710/72 |
| 2004/0263351 A1 | 12/2004 | Joy et al. | | |
| 2010/0004863 A1 * | 1/2010 | Ladow et al. | ...................... | 702/3 |
| 2010/0128751 A1 * | 5/2010 | Doll | ............................... | 374/28 |
| 2010/0305718 A1 * | 12/2010 | Clark et al. | ..................... | 700/17 |

FOREIGN PATENT DOCUMENTS

| | | |
|---|---|---|
| DE | 202004004775 U1 | 8/2004 |
| DE | 20122317 U1 | 2/2005 |
| DE | 102004007341 A1 | 9/2005 |
| EP | 1 302 831 A2 | 4/2003 |
| WO | WO 02/33395 A1 | 4/2002 |

* cited by examiner

*Primary Examiner* — Yaritza Guadalupe-McCall
(74) *Attorney, Agent, or Firm* — Walter A. Hackler

(57) ABSTRACT

A sensor arrangement comprises a dew point sensor for measuring the dew point characteristic in a room, and a temperature sensor for measuring the temperature characteristic on a wall surface of the room, means being provided for evaluating and/or storing the measured dew point characteristic and the measured wall surface temperature characteristic.

8 Claims, 2 Drawing Sheets

SENSOR ARRANGEMENT

The present invention relates to a sensor arrangement for a room, or rather a wall surface of the room. The term "room" can be construed broadly in the context of the invention. A room is not necessarily to be understood as being a closed space. The room may be a dwelling, a motor vehicle, a cavity, a chimney or the like.

Sensor arrangements are used, for example, in museums in order to be able to recognise at an early stage any room climate influences that are detrimental to the museum exhibits. For this purpose, the air humidity characteristic and the air temperature characteristic measured by the temperature sensor are normally stored, or documented, on a storage medium, for example a roll of paper. Such sensor arrangements are of only limited suitability for determining a mould-forming tendency in rooms, since mould forms on wall surfaces of the rooms, that is to say, on the ceiling, a wall or on the floor of a room, and the mentioned sensor arrangements record only the air humidity and the air temperature in the interior of the room.

In motor vehicles, sensor arrangements are used in the vehicle passenger space for monitoring a moisture condensation tendency, especially of the vehicle windscreen. Such sensor arrangements comprise a dew point sensor having an air humidity sensor element and a temperature sensor, the air humidity sensor element and the temperature sensor being coupled thermally. The temperature sensor is used as a surface temperature sensor, for example, of the windscreen.

EP1380481 A2 and EP1306242 A1 propose fitting an air humidity sensor element directly on or in the immediate vicinity of the windscreen. This sensor element measures the relative air humidity. From the data obtained therefrom, conclusions are drawn as to the tendency of the screen to mist up. Furthermore, EP1306242 A1 proposes that the temperature in the passenger space of a motor vehicle should also be taken into account in order to prevent misting-up.

WO 02/33395 A1 discloses a dew point sensor. If heat is withdrawn from a gaseous medium, for example steam, as may happen, for example, on the inner surface of a motor vehicle window, the medium condenses at a relevant temperature to form a liquid, for example water. This is referred to as falling below the dew point. The temperature at which the liquid condenses (dew point temperature) and the associated relative air humidity are called the dew point. If, at a specific relative air humidity, the temperature at a surface is close to the dew point temperature or if this surface temperature falls below the dew point temperature, the surface tends to become misted up (moisture condensation tendency), that is to say, the liquid condenses out on the surface.

The dew point sensor comprises a mounting base on which an air humidity sensor and an air temperature sensor are arranged. A thermally conductive coating which contacts the air humidity sensor and the air temperature sensor thermally is applied to the mounting base. Since the air humidity sensor and the air temperature sensor acquire data at the same temperature owing to the thermal contacting, it is possible to ascertain from the acquired data of the sensors, at the site of the mounting base of the dew point sensor, whether the dew point has been reached, that is to say, whether at the measured temperature the measured air humidity is above the air humidity of the dew point or whether at the measured air humidity the measured temperature is below the dew point temperature. The known sensor arrangements having dew point sensors do not record the measured air humidities and surface temperatures.

The object of the invention is to provide a sensor arrangement for a room which avoids the disadvantages of the prior art; in particular it is to be possible to determine in a reliable manner a mould-forming tendency in the region of a wall surface or on a wall surface of the room.

SUMMARY OF THE INVENTION

This object is achieved by a sensor arrangement according to patent claim 1. The dependent claims represent preferred embodiments of the invention.

A sensor arrangement according to the invention is suitable for determining a mould-forming tendency in at least one room, for example in a building.

The dew point sensor and one or more temperature sensors can be combined to form a measuring device or can merely form an arrangement composed of a dew point sensor and one or more temperature sensors, the sensors being uncoupled from each other.

The sensor arrangement according to the invention enables the dew point characteristic and a wall temperature characteristic to be recorded. This permits reliable determination of a mould-forming tendency on the wall in the region of which the wall temperature characteristic is measured. For this purpose, use is made of a dew point sensor arrangement which has a similar structure to that of known dew point sensor arrangements used in motor vehicles to measure the tendency of the windscreen to mist up. Since the mould-forming tendency of a wall depends on the humidity of the wall and therefore on the tendency of the water present as steam in the ambient air to liquefy on the wall, that is to say, to precipitate on the wall, the room climate data relevant to the precipitation are measured and stored, or documented, by means of the sensor arrangement according to the invention. These room climate data are the values of the quantities determining the dew point at the wall, namely the air humidity and the temperature of the wall. If the temperatures of the measured wall temperature characteristic fall permanently or at least frequently below the dew point temperature of the associated air humidity, that is to say, the air humidity measured at the time of the temperature measurement, there is a high probability of mould formation on the wall on which the wall temperature characteristic was measured because moisture can then precipitate there. Falling below the dew point temperature is also even understood to mean falling below a temperature range of the dew point. This temperature range may even lie a few degrees Celsius above the actual dew point temperature because, even then, moisture from the wall dries up only very slowly.

By means of the sensor arrangement according to the invention, the room climate data can be recorded over a relatively long period of time, for example several weeks or months. As a result, the room climate, and especially also the ventilation behaviour, can be monitored. Therefore, for example, disputes between landlords and tenants as to the causes of mould formation can be settled.

If the data ascertained by means of the processes according to the invention are used as a basis for controlling a heating system or an air-conditioning system, the room climate can be regulated in a controlled manner to avoid mould formation. For example, in a motor vehicle a rear window heating system can be controlled. Effective heating can be achieved by means of the invention. For example, heating members, such as heating foils, heating wires or also insulating materials, can be arranged on the wall surfaces to be monitored. This may apply especially to heating members behind cupboards or behind structural elements.

The sensor arrangement according to the invention may be in the form of a mobile device or may be installed in a fixed manner in a building or a motor vehicle.

Preferably, an evaluation unit is provided which is set up to store a mould-forming tendency indicator in the storage module when the wall temperature characteristic falls below a dew point temperature of a dew point of the air in the interior volume space of the room or below a predetermined temperature limit. For the reasons mentioned above, the temperature limit may be a few degrees Celsius above the dew point temperature.

As a result, the measured data can be evaluated in an automated manner. Information is stored directly as to whether at the mounting site, that is to say, the wall, on which the sensor arrangement according to the invention is positioned, there is an increased probability of mould formation.

If the evaluation unit is set up to emit an alarm signal when the dew point temperature is fallen below at a mounting site of the temperature sensor, mould formation can be actively combated by suitable counter-measures, for example ventilation or heating.

Especially preferably, the dew point sensor arrangement is arranged in a housing, a data transfer interface, preferably a wireless communication interface, especially a Bluetooth interface, and/or a connector interface, especially a USB interface, being provided on the housing. The sensor arrangement according to the invention can therefore be used in a simple manner together with a commercially available computer to display the measured data and/or to evaluate those data. For this purpose, only driver and evaluation software has to be installed in the computer. It is not necessary to lay any cables in order to use the sensor arrangement.

If the housing is formed at least partly by a moisture-permeable membrane or has air passage holes, reliable measurement of the air humidity characteristic in the interior volume space of the room is possible because the ambient air can circulate well around the air humidity sensor element.

Advantageously provided are adhesives or means for the releasable securing of the temperature sensor to the wall, as a result of which the sensor arrangement according to the invention can be handled in an especially simple manner.

Preferably, a thermal uncoupling of the temperature sensor from the air humidity sensor element is provided for. The temperatures of the walls of a room often do not correspond to the temperature of the interior volume because the walls warm up or cool down only slowly when the temperature of the interior changes. As a result, a measurement of the air humidity characteristic in the interior volume space of the room may be falsified if the air humidity sensor element is kept at the temperature of the wall. This is especially true when the relative air humidity is measured directly by the air humidity sensor element. The thermal uncoupling therefore permits more reliable determination of any falling below the dew point at the measured air humidity.

Preferably, an interior temperature sensor is provided which is set up to measure an interior temperature characteristic in the interior volume space of the room. This interior temperature sensor measures the temperature which the air humidity sensor element of the dew point sensor arrangement also exhibits. It is thus possible to carry out in a reliable manner the ascertaining of the relative air humidity, which is necessary to establish that the dew point has been fallen below, without the possibility of an error occurring owing to the use of the wall temperature to ascertain the relative air humidity. Furthermore, from the changes in the interior temperature characteristic, conclusions can be drawn as to the ventilation behaviour in the room.

A building management control centre according to the invention has at least one sensor arrangement according to the invention. Data acceptance means are provided for accepting the measured wall temperature characteristics and the measured air humidity characteristics of the sensor arrangement. The data acceptance means are preferably in the form of a wireless communication interface, especially a Bluetooth interface, and/or a connector interface, especially a USB interface. A mould-forming tendency indicator can be displayed using output means. The measuring points for measuring wall temperature characteristics are to be provided in regions of the building where a mould-forming tendency is expected.

The sensor arrangement according to the invention is suitable for determining a mould-forming tendency in a room of a building, that is to say, on an interior wall of the room.

BRIEF DESCRIPTION OF THE DRAWINGS

The invention can also be used to prevent the external misting-up of glass panes or glass facades.

Further advantages will emerge from the description and the appended drawings. The above-mentioned features of the invention, and those indicated below, can be used individually or in combination with one another. The mentioned embodiments are not to be understood as a definitive list but, rather, are in the nature of examples.

The invention will be explained in more detail hereinafter by means of embodiments with reference to the drawings.

Figure 1:
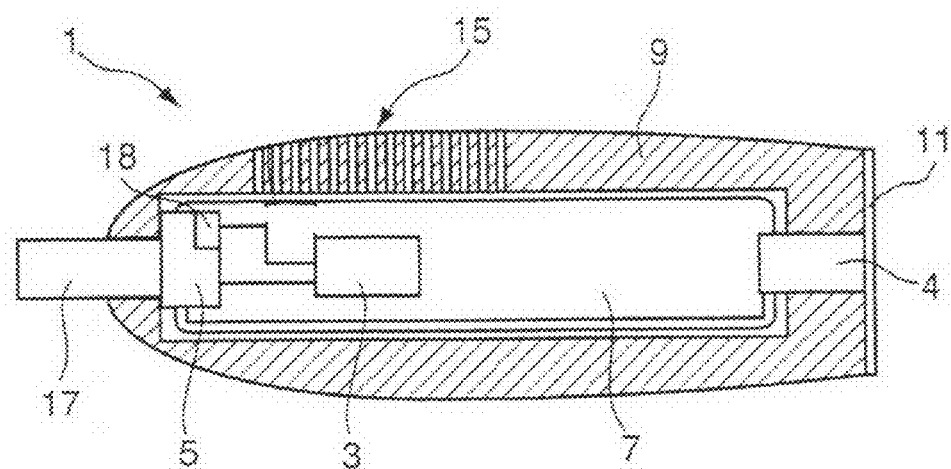
Figure 2:
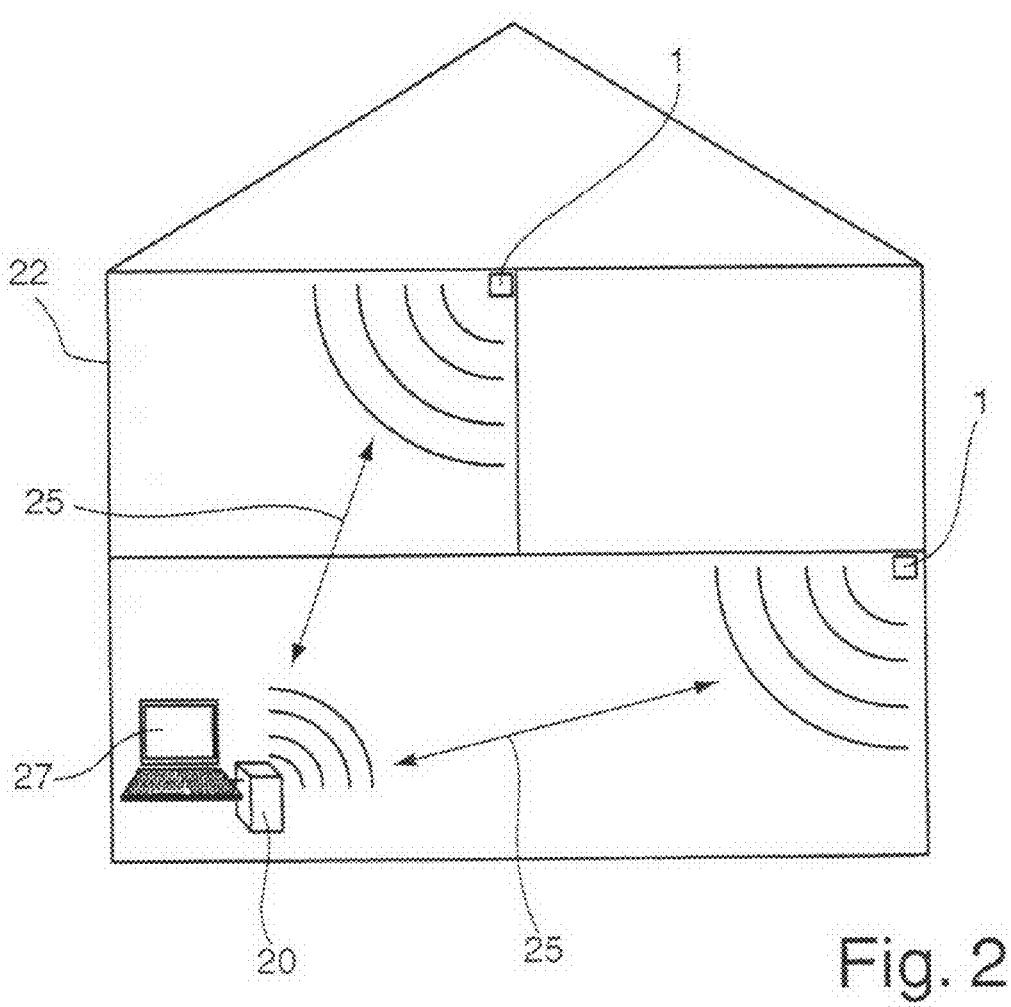
Figure 3:
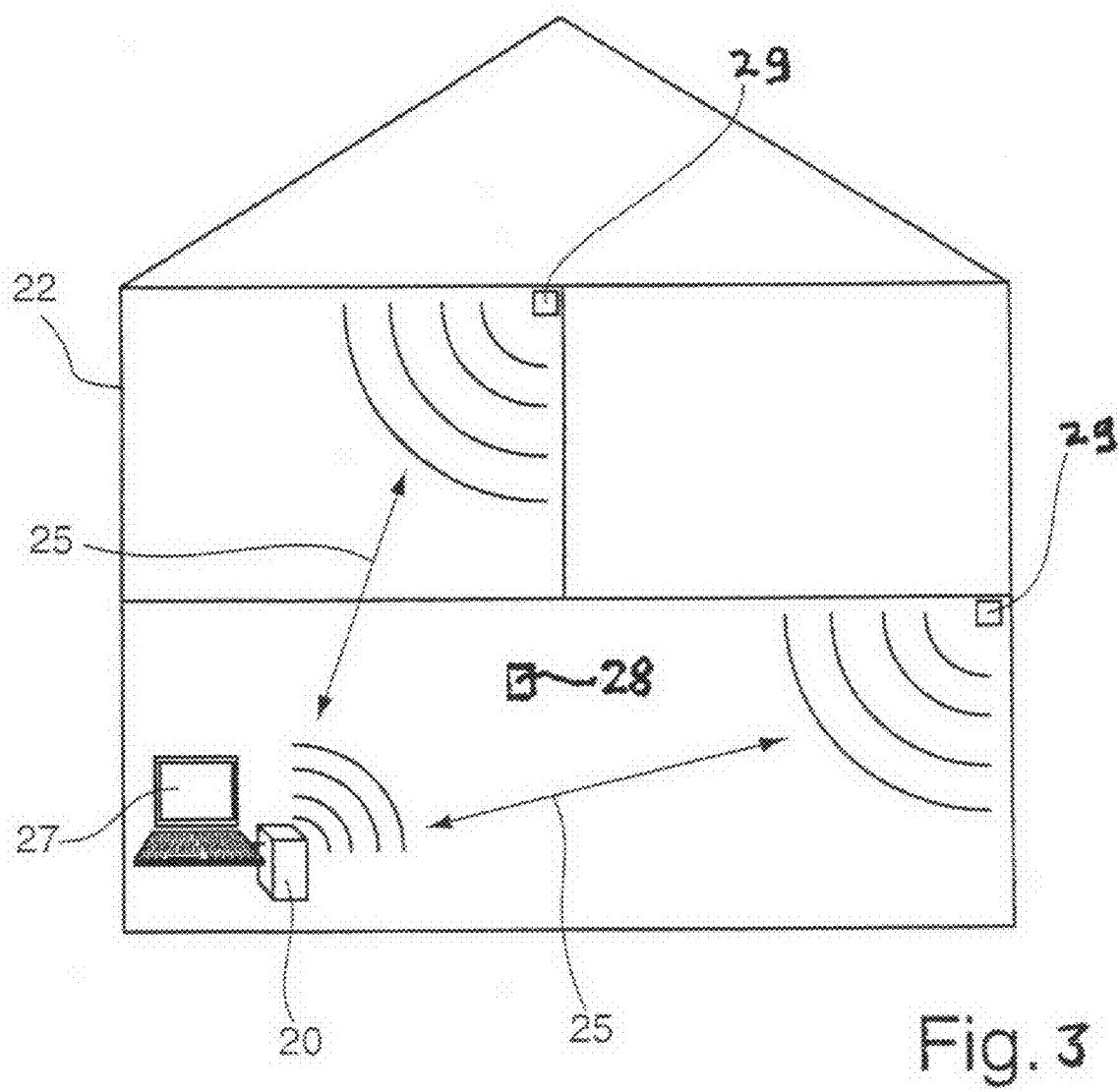

FIG. 1 shows a sensor arrangement which is in the form of a USB plug-in device (USB stick);

FIG. 2 shows a building management control centre in conjunction with the sensor arrangement according to FIG. 1;

FIG. 3 shows a building management control centre in conjunction with a further sensor arrangement.

DETAILED DESCRIPTION

FIG. 1 shows a sensor arrangement 1 according to the invention which is in the form of a USB plug-in device. A dew point sensor 3 for measuring the dew point characteristic, and a temperature sensor 4 for measuring a wall temperature characteristic are secured, together with a storage module 5 for storing the measured dew point characteristic and the measured wall temperature characteristic, on a mounting base 7, for example a board.

The board with the dew point sensor 3 is arranged inside a housing 9. The temperature sensor 4 is positioned in a housing wall so that the temperature sensor 4 can be brought into contact with, for example, a wall of a room, so that the wall temperature characteristic can be measured correctly by means of the temperature sensor 4. In the region of the temperature sensor 4 provided for measuring the wall temperature, adhesives 11 are provided on the outside of the housing in order to secure the sensor arrangement 1 to the wall on which, for example, a mould-forming tendency is to be determined. These adhesives may be, for example, in the form of a coating of gum. Furthermore, means for releasable attachment are possible.

In addition, an energy source, for example a battery, is to be provided in the housing for the supply of energy.

The dew point sensor 3 comprises an interior temperature sensor and an interior air humidity sensor element. The interior temperature sensor is in thermal contact with the air humidity sensor element. The air humidity sensor element is at a distance from the temperature sensor 4 which is to be positioned in the region of a wall surface, and therefore measures an interior air humidity. Therefore, by means of the interior temperature sensor 13, it is possible to measure an associated interior temperature characteristic in the interior volume space of a room. In order to permit as exact a measurement as possible of the interior air humidity and/or of the interior temperature characteristic, air passage holes 15 are provided in the housing 9 in the region of the air humidity sensor element and/or the interior temperature sensor. The dew point characteristic can therefore be recorded by means of the dew point sensor 3. The temperature characteristic at the building wall can be recorded by means of the temperature sensor 4. The dew point sensor 3 and the temperature sensor 4 are together integrated to form an arrangement which forms the basis for a compact measuring device.

The sensor arrangement 1 has on its housing 9 a data transfer interface 17 which is in the form of a USB connector interface, that is to say, in the form of the male connector of a USB connector interface. By means of the data transfer interface 17, the dew point characteristic measured by the dew point sensor arrangement and stored in the storage module, and the wall surface temperature characteristic can be read out of the storage module 5 and transferred to an evaluation unit, for example a computer. By means of the evaluation unit, a mould-forming tendency on the wall surface on which the sensor arrangement 1 was secured can be ascertained from the measured characteristics. This tendency exists when the measured temperature characteristic on the wall surface drops below the dew point characteristic.

An evaluation unit 18 is provided. This is set up to store a mould-forming tendency indicator in the storage module 5 when the wall temperature characteristic falls below a dew point temperature of a dew point of the air in the interior volume space of the room or a predetermined temperature limit.

FIG. 2 shows a building management control centre according to the invention. The building management control centre has a computer 20 and several sensor arrangements 1 according to the invention. The sensor arrangements 1 are each secured in a corner of a respective room of a building 22 on a wall of that room. The computer 20 communicates in a wireless manner with the sensor arrangements 1. The sensor arrangements 1 may be constructed, for example, as shown in FIG. 1, a wireless communication interface, for example a Bluetooth interface, additionally being provided in the housing. The wireless communication 25 symbolised in the Figure by double arrows is used to transmit the temperature characteristics and interior air humidity measured by the sensor arrangements 1 to the computer 20 which acts as an evaluation unit. The screen of the computer 20 acts as the output means 27 for outputting a mould-forming tendency indicator.

FIG. 3 shows a further building management control centre according to the invention. The building management control centre has a computer 20, a dew point sensor 28 and several temperature sensors 29. The temperature sensors 29 are each secured in a corner of a respective room of a building 22 on a wall of that room. The computer 20 communicates in a wireless manner with the sensors 1. The wireless communication 25 symbolised in the Figure by double arrows is used to transmit the characteristics measured by the sensors to the computer 20 which acts as an evaluation unit. The screen of the computer 20 acts as the output means 27 for outputting a mould-forming tendency indicator.

What is claimed is:

1. Sensor arrangement for determining mould-forming tendency of a wall of a room, the arrangement comprising:
   a dew point sensor for measuring a dew point characteristic in the room;
   a temperature sensor for measuring a temperature characteristic on a wall surface of the room;
   means for evaluating and/or storing the measured dew point characteristic and the measured wall surface temperature characteristic; and
   an evaluation unit for storing a mould-forming tendency indicator in a storage module when the wall temperature characteristic falls below a dew point temperature of a dew point of the air in an interior volume space of the room or a predetermined temperature limit.

2. Sensor arrangement according to claim 1, wherein the evaluation unit is operative for controlling a heating system when the dew point temperature falls below the dew point temperature.

3. Sensor arrangement according to claim 1, wherein the evaluation unit is operative for emitting an alarm signal when the dew point temperature falls below a mounting site temperature sensor.

4. Sensor arrangement according to claim 1, wherein the dew point sensor is arranged in a housing, and the sensor arrangement further comprises a data transfer interface having a wireless communication interface, and/or a connector interface, disposed on the housing.

5. Sensor arrangement according to claim 4, wherein the housing is formed at least partly by a moisture-permeable membrane or air passage holes.

6. Sensor arrangement according to claim 1, further comprising adhesives for securing the temperature sensor to the wall surface.

7. Building management control center having at least one sensor arrangement according to claim 1, further comprising data acceptance means for accepting the measured wall temperature characteristics and the measured air humidity characteristics of the sensor arrangement and output means for outputting a mould-forming tendency indicator.

8. Use of the sensor arrangement according to claim 1 for determining a mould-forming tendency in a room of a building.

* * * * *